United States Patent [19]

Rieder

[11] Patent Number: 5,043,010

[45] Date of Patent: * Aug. 27, 1991

[54] PROCESS FOR PROLONGING THE DORMANCY OF PLANTS OR PLANT PARTS

[75] Inventor: Georg L. Rieder, Stein/Traun, Fed. Rep. of Germany

[73] Assignee: SKW Trostberg Aktiengesellschaft, Trostberg, Fed. Rep. of Germany

[*] Notice: The portion of the term of this patent subsequent to Dec. 11, 2001 has been disclaimed.

[21] Appl. No.: 261,767

[22] Filed: Oct. 24, 1988

Related U.S. Application Data

[63] Continuation of Ser. No. 945,188, Dec. 23, 1986, abandoned, which is a continuation of Ser. No. 804,693, Dec. 4, 1985, abandoned.

[30] Foreign Application Priority Data

Dec. 4, 1984 [DE] Fed. Rep. of Germany ....... 3444211

[51] Int. Cl.$^5$ ............................................. A01N 33/02
[52] U.S. Cl. ......................................... 71/121; 71/77; 71/65
[58] Field of Search ........................ 71/65, 55, 77, 121

[56] References Cited

U.S. PATENT DOCUMENTS 4,487,685 12/1984 Rieder ..................................... 71/77

FOREIGN PATENT DOCUMENTS

B13130 5/1984 Australia .
3150404 6/1983 Fed. Rep. of Germany .

OTHER PUBLICATIONS

Chem. Abst., vol. 14 (1920), p. 292-D, Mazé, et al., "The Action of Cynamide . . . .".
Chem. Abst., vol. 56 (1962), 2729i, Rotini, et al., "Antimitotic Action of Cyanamide an Sev Cultivated Plts".
Kuwabara, "Whole Bud Growth Experiment Using Plant Growth Regulators", C. A. vol. 88, 184472b, 1978.

Primary Examiner—Richard L. Raymond
Assistant Examiner—Brian M. Burn
Attorney, Agent, or Firm—Felfe & Lynch

[57] ABSTRACT

The present invention provides a process for prolonging the dormancy of plants or plant parts, wherein the plants or plant parts are treated with an aqueous cyanamide solution before the anticipated sprouting.

7 Claims, No Drawings

PROCESS FOR PROLONGING THE DORMANCY OF PLANTS OR PLANT PARTS

This application is a continuation of Ser. No. 945,188, filed Dec. 23, 1986, now abandoned, which is a continuation of Ser. No. 804,693, filed Dec. 4, 1985, now abandoned.

FIELD OF THE INVENTION

The present invention is concerned with a process for prolonging the dormancy of plants or plant parts, as well as with a method for the prevention of late frost damage to plants.

BACKGROUND AND PRIOR ART

As is known, the development of plants takes place in different stages which are clearly distinct. Examples of such stages are the germination of seeds, the sprouting of perennial plants, the formation of leaves and blossoms and the formation of fruits and seeds. This course of development is genetically determined and is thus influenced by internal, so-called endogenic growth factors.

These endogenic growth factors, however, are in reciprocal relationship to external, i.e. exogenic, growth factors. Examples of these are light, temperature, air, water and nutrients.

Actively growing plants are not very resistant to unfavorable external growth factors such as frost, heat or insufficient water. For the preservation of the species, the plants protect themselves against such fatal external conditions in that the plant parts necessary for the survival of the plants, for example seeds, root stocks, rhizomes, bulbs or buds, pass over into a quiescent stage, the so-called dormancy period. In this state of dormancy, the plants show no externally visible growth, i.e., no sensitive plant parts are formed which could be damaged by unfavorable external conditions.

The beginning and end and thus the period of the dormancy are essentially controlled by environmental factors, such as those set forth supra.

A prolongation of the dormancy offers decisive advantages for the practical cultivation of plants, especially in fruit and grape growing. These advantages are of importance especially under those climatic conditions in which there is still a danger of frost after the commencement of active growth. Such late frosts, which do not occur regularly or with equal severity every year, cause damage to fruit trees and grape vines which have already sprouted and this always involves considerable crop losses.

Attempts have been made to prevent such late frost damage (cf. in this regard, R. I. Weaver, "Grape Growing", pp. 47-55, pub. John Wiley & Sons, N.Y., 1976). Such methods include so-called "frost sprinkling", i.e., the influence of layers of cold air circulated by wind blowers, or the direct heating of orchards. All these methods, which are directed towards the protection of buds and leaves which have already sprouted, are either of only limited effectiveness or are uneconomical because of high energy costs.

Attempts have also been made to prevent late frost damage by prolongation of the dormancy phase with the help of plant hormones (cf. R. I. Weaver, "Plant Growth Substances in Agriculture", pp. 166-167, pub. W. H. Freeman & Co., 1972). Thus, for example, experiments have been carried out with natural plant hormones, such as gibberellin or abscisin, and with synthetic growth inhibitors, such as chlorocholine chloride. These have not given the desired results.

It is, therefore, an object of the present invention to provide a process for prolonging the dormancy of plants or plant parts.

According to the present invention, there is provided a process for prolonging the dormancy of plants or plant parts, wherein the plants or plant parts are treated with an aqueous cyanamide solution before the anticipated sprouting of the plant or plant part.

We have, surprisingly, ascertained that by means of the process according to the present invention, it is possible to achieve considerable prolongation of the dormancy phase. This was surprising because, according to the prior art (see Federal Republic of German Patent Specification No. 31 50 404), a cyanamide solution had precisely the opposite effect, namely, the termination of bud dormancy.

In the case of the process according to the present invention, the cyanamide solution is applied before the anticipated sprouting to plants or plant parts to be treated. Examples of plant parts which can be so treated are buds, rhizomes, corms, bulbs or root stock. The optimum time of treatment is from about 4 weeks to immediately, i.e., about 1 day, before the anticipated sprouting, the time of treatment having a decisive influence on the prolongation of the dormancy. The later the treatment takes place, i.e., the shorter the period of time between treatment and anticipated sprouting, the longer is the delay of the sprouting. In the most favorable case, the prolongation of the dormancy can be up to 14 days. Thus, with the help of the process according to the present invention, it is possible not only to prolong the dormancy in general but also positively to control the period of prolongation by means of the point of time at which the treatment is carried out.

The aqueous cyanamide solution used preferably has a concentration of about 0.05 to about 10% by weight and more preferably of about 1 to about 3% by weight. The cyanamide solution can be applied by means of conventional spraying apparatus and thus has the advantage of a problem-free and readily measurable application.

The amount of cyanamide solution used is preferably such that a complete wetting of the plants or plant parts to be treated takes place. Wetting agents, especially alkylaryl polyglycol ethers, for example "Citowett", may be added to the cyanamide solution, preferably in an amount of from about 0.1 to about 1% by weight, referred to the cyanamide solution.

The process according to the present invention is suitable for the treatment of all plants and especially of fruit trees and grape vines.

The important advantages of the process according to the present invention are the objective control of the prolongation of the dormant phase, simple handling and great economy since cyanamide is an inexpensive chemical. These advantages are the important prerequisites for a safe and economic method for preventing or substantially avoiding crop losses due to late frosts.

DETAILED DESCRIPTION OF PREFERRED EMBODIMENTS

The following Examples are given for the purpose of illustrating the present invention:

EXAMPLE 1

The vine type "Nobling" is known in the South Baden wine-growing region for poor sprouting. Furthermore, late frosts occur frequently in that area which, after sprouting, can lead to considerable damage. According to practical experience, sprouting in the experimental year was expected about the 10th May. The cyanamide solution according to the present invention was sprayed on in a concentration of 2.5% by weight on the 24th April, i.e., only 15 days before the anticipated sprouting. The delay of sprouting was about 10 days, as can be seen from the following Table 1:

TABLE 1

Influence of cyanamide on the prolongation of the vine type "Nobling", measured by the date of sprouting

| treatment | date of sprouting | prolongation of the dormant period |
| --- | --- | --- |
| untreated | 10th May | — |
| 2.5% cyanamide solution on the 24th April | 20th May | 10 days |

EXAMPLE 2

The Aconcagua Valley in South America is a relatively recent wine-growing area. At the time of normal bud sprouting, there are greatly varying day and night temperatures. Whereas the afternoon temperature can increase to beyond 20° C., it is possible that temperatures in the region of freezing point can occur during the night.

Experiments for the prolongation of the dormant period were carried out with Thompson Seedless, the most important vine type in that region. An aqueous solution of cyanamide with a concentration of 2.5% by weight was sprayed on at different times. According to practical experience, normal sprouting is expected to take place on the 28th August. Consequently, the treatment times were fixed for 15 to 0 days before the expected sprouting. Indeed, the first manifestations of bud sprouting, i.e., swelling of the buds and visibility of the hairs of the first leaves (cotton stage), were already observed on the 28th August. This means that in the case of the latest date of application, the cyanamide was sprayed on directly at the end of the dormant period. As can be seen from the following Table 2, the late application resulted in a 10 day prolongation of the dormancy.

TABLE 2

Influencing the prolongation of the dormant phase of the vine type "Thompson Seedless" in the Aconcagua Valley

| treatment | date | days before expected sprouting | sprouting date | prolongation of the dormant period in days |
| --- | --- | --- | --- | --- |
| untreated | — | — | 28th August | — |
| 2.5% cyanamide solution | 15th August | 15 | 29th August | 1 |
| | 28th August | 0 | 13th September | 10 |

The simplicity of the method herein described lends itself to application to different crops, as will be evident to one skilled in the art. The concentration used, and the time of application will of course vary, depending upon the crop.

It will be understood that the specification and examples are illustrative but not limitative of the present invention and that other embodiments within the spirit and scope of the invention will suggest themselves to those skilled in the art.

I claim:

1. The method of prolonging the bud dormancy of grape vines, which comprises contacting said grape vines from four weeks to one day prior to the sprouting of said grape vines with an aqueous cyanamide solution containing an effective bud dormancy prolonging amount of cyanamide.

2. The method of claim 1, wherein the concentration of cyanamide in said cyanamide solution is from about 0.05 to about 10% by weight.

3. The method of claim 1, wherein the concentration of cyanamide in said cyanamide solution is from about 1 to about 3% by weight.

4. The method of claim 1, wherein the grape vines are completely wetted with said cyanamide solution.

5. The method of claim 1, wherein said cyanamide solution also contains a wetting agent.

6. The method of claim 5, wherein the concentration of the wetting agent is from about 0.1 to about 1% by weight of the cyanamide solution.

7. The method of claim 5, wherein the wetting agent is alkyaryl polyglycol ether.

* * * * *